United States Patent [19]

Kessler et al.

[11] Patent Number: 5,629,024
[45] Date of Patent: May 13, 1997

[54] METHOD OF FORMING AN IODINE BASED GERMICIDE COMPOSITION

[75] Inventors: Jack H. Kessler, Southborough; Rick Panicucci, Lexington; John J. Hickey, Weymouth, all of Mass.

[73] Assignee: Symbollon Corporation, Sndbury, Mass.

[21] Appl. No.: 293,283

[22] Filed: Aug. 22, 1994

[51] Int. Cl.$^6$ .................. A61K 31/74; A61K 38/43; A61K 33/36

[52] U.S. Cl. .................. 424/667; 424/70.15; 424/78.02; 424/78.05; 424/94.1; 424/668

[58] Field of Search .................. 424/78.05, 94.4, 424/70.15, 78.02, 94.1, 667, 668, 669

[56] References Cited

U.S. PATENT DOCUMENTS

| | | | |
|---|---|---|---|
| 2,900,305 | 8/1959 | Siggia | 167/70 |
| 3,028,300 | 4/1962 | Contor et al. | 167/17 |
| 4,271,149 | 6/1981 | Winicov et al. | 424/150 |
| 4,320,114 | 3/1982 | Denzinger et al. | 424/80 |
| 4,370,199 | 1/1983 | Orndorff | 162/161 |
| 4,576,817 | 3/1986 | Montgomery | 424/94 |
| 4,937,072 | 6/1990 | Kessler | 424/94.4 |
| 4,996,146 | 2/1991 | Kessler | 435/28 |
| 5,169,455 | 12/1992 | Kessler | 134/42 |
| 5,227,161 | 7/1993 | Kessler | 424/94.4 |

OTHER PUBLICATIONS

Iodation des Prottenes par voie enzymatique by Nunez & Pommier European Journal of Biochemistry vol. 7 pp. 286–293 1969.

Peroxidase catalyzed Halogenation Morrison & Schonbaum Annual Review of Biochemistry vol. 45 pp. 861–888 1976.

Analyses of Catalytic Intermediates of Hog Thyroid Peroxidase etc. Ohtaki, Nakagawa, Kimura and Yamakazi Journal of Biochem. vol. 256 pp. 805–810 1981.

*Primary Examiner*—John W. Rollins
*Assistant Examiner*—Deborah K. Ware

[57] ABSTRACT

Germicidal iodine based compositions are disclosed that consist of iodide anions, a source of peroxide and peroxidase in combination with iodine sequestering agents. The compositions are formed in situ in an aqueous based medium by combining a peroxide source, iodine ions or source thereof, a peroxidase classified within Enzyme Commission identification No. E.C. 1.11.1.7 and an iodine sequestrant. The addition of a sequestrant before the equilibration of the enzymatic reaction formed by admixing the composition with an aqueous based medium, provides for a non-reactive enzymatic composition. The resulting composition having an increase of available iodine concentration compared to an identical composition without an iodine sequestrant.

9 Claims, No Drawings

METHOD OF FORMING AN IODINE BASED GERMICIDE COMPOSITION

FIELD

This invention relates to an enzymatic iodine based germicide and more particularly to an iodine based germicide formed from (1) a source of iodide or aqueous iodide anions, (2) peroxidase, (3) a source of peroxide and (4) chemical agents that complex iodine. Another term for an agent that complexes iodine is an iodine sequestrant. In accordance with the present invention it has been observed that iodine sequestrants under appropriate conditions will increase the levels of available iodine in a peroxidase based iodine disinfectant.

Additionally, it has been observed that certain sequestrants can extend the period of time that a germicide composition comprised of iodide anion, peroxide and peroxidase will maintain a defined concentration range of available iodine. Increased available iodine and extended stability are accomplished in accordance with the present invention by the selective addition of iodine sequestering agents. This teaching is particularly advantageous for use with a germicidal iodide/peroxide/peroxidase based composition having available iodine levels between 0.0025 and 0.5%.

INTRODUCTION

It is known from Kessler (U.S. Pat. No. 4,227,161, U.S. Pat. No. 5,169,455, U.S. Pat. No. 4,996,146 and U.S. Pat. No. 4,937,072), Orndoff(U.S. Pat. No. 4,370,199) and Montgomery (U.S. Pat. No. 4,576,817) that a combination of peroxidase, peroxide and iodide anions will form a bactericide in an aqueous environment. The bactericidal efficacy of this combination results from the enzymatic reaction that occurs when peroxidase, hydrogen peroxide and iodide react in solution. Peroxidase is known to effect the transfer of electrons from iodide to hydrogen peroxide. Hydrogen peroxide is converted into water by this reaction. Several possible reaction products have been postulated for the iodide anion that serves as an enzyme substrate including: 1) iodine free radicals (Nunez and Pommier, *European Journal of Biochemistry*, volume 7, pages 286–293, 1969); 2) hypoiodite ion (Morrison and Schonbaum, *Annual Review of Biochemistry*, volume 45, pages 861–888, 1976); and 3) iodinium ion (Ohtaki, Nakagawa, Kimura and Yamakazi, *Journal of Biochemistry*, volume 256, pages 805–810, 1981).

The enzymatic reaction products of iodide, whatever their identity, would have the capacity to react with each other and/or other compounds that are in the immediate environment. These enzymatic reaction products and/or by-products of the enzymatic reaction products could contribute to the antibacterial efficacy of these compositions. Whether the enzymatic reaction products themselves or by-products of the enzymatic reaction products (or some combination thereof) are present, it has been observed that under certain conditions these reactions will generate significant levels of molecular iodine and other forms of thiosulfate titrable iodine such as triiodide. Thiosulfate titration of iodine is the analytical method currently used to characterize iodine concentration in regulatory submissions and label claims for iodine-based germicides. The phrase "available iodine" is a term of art that refers to an iodine determination that is accomplished by titrating an unknown sample with sodium thiosulfate.

It has been observed that it is possible to generate levels of available iodine that are equivalent to those used in commercial iodine-based disinfectants and sanitizers using compositions of peroxidase, peroxide and iodide. The exact level of available iodine in these compositions is a function of the concentration levels of peroxide, iodide, peroxidase, buffering agents, pH and other additives. The level of available iodine in commercial iodine germicides is an essential parameter for regulatory compliance, efficacy and consumer acceptance. The primary component of raw material cost in commercially available iodine germicides is typically the cost of iodine/iodide. Since iodine-based germicides are specialty chemicals, cost is a critical aspect for product acceptance.

SUMMARY OF THE INVENTION

A germicidal iodine based composition is formed the combination of iodide anions, peroxide, peroxidase and iodine sequestering agents. Iodine sequestrants have traditionally been employed to (1) increase the shelf-life of iodine-based preparations and (2) mitigate unpleasant toxicological and organoleptic effects of iodine. Iodine sequestrants do not increase the level of available iodine in non-enzymatic compositions. In fact, inclusion of a sequestrant in an aqueous iodine preparation is expected to effect a decrease in the level of available iodine. Some iodine sequestrants bind molecular iodine and some sequestrants, like polyvinylpyrrolidone, predominantly bind triiodide. Theoretical and experimental observations suggest that available iodine levels are not increased by the inclusion of an iodine sequestrant. Contrary to what one skilled in the art would anticipate it has been discovered that the level of available iodine in a peroxidase, peroxide and iodide composition can be increased by the inclusion of an iodine sequestrant.

Not all of the commonly used iodine sequestering agents are useful in increasing the level of available iodine generated from the iodide anion/peroxide/peroxidase system. In fact, some of the iodine sequestrants can significantly reduce the level of available iodine in these compositions which would be highly undesirable and lead to a less effective and/or a more costly composition. Accordingly, this application identifies the preferred iodine sequestering agents and a method to: (1) increase the level of available iodine and/or (2) extend the stability of such compositions in an aqueous environment.

DESCRIPTION

This application describes iodine-based products based upon the iodine sequestrants, iodide anion, peroxide and peroxidase system that have increased available iodine and/or increased stability relative to the identical formulations without iodine sequestrants. The products contemplated under this application all utilize peroxidase, peroxide, iodide anions in combination with iodine sequestrants as defined herein; these four agents will typically be combined with other compounds to provide other desirable product attributes as required. These additional agents include the following classes of compounds: organic detergents, humectants, emollients, small molecules with surface active activity, buffers, surfactants, solvents, foam stabilizers, thickeners, buffering agents, microspheres or liposomes of organic or inorganic materials and enzyme stabilizers.

Products contemplated under this application will be stored or packaged in an "unreacted state" prior to use. An unreacted state is defined as conditions which prevent the peroxidase catalyzed reaction between iodide and peroxide or the chemical oxidation of iodide or the chemical reduction of peroxide.

The compositions of this application are reconstituted in an aqueous environment some period of time prior to the intended use and the enzyme reaction then generates the required level of iodine. One method of packaging is to compartmentalize a source of peroxide in one chamber of a package and to include iodide anions in another chamber of a package. Selected components can be placed in a separate compartment if they prove to be incompatible with other components. It is possible to include a liquid as one of the components provided that the liquid components are maintained separately from the other components prior to use.

Iodine sequestering agents are an integral part of this invention in that it is their use that is contemplated to extend the solution stability of iodine generated by the iodide anion, peroxide and peroxidase system and/or to increase the levels of thiosulfate titrable iodine. Iodine sequestrants or complexing agents are well known in the art and examples can be found in U.S. Pat. Nos. 2,931,777; 2,759,869; 3,028,300 and many others. Examples of iodine complexing agents include nonionic poly(ethylene oxide) homopolymers such as Polyox N-10 and Polyox N-12K where Polyox is a trade name of Union Carbide; block copolymers of ethylene oxide and propylene oxide such as Pluronic F-38, Pluronic F68, Pluronic F 87 Prill, Pluronic F108 Prill, Pluronic 25 R4, Pluronic P-105 where pluronic is a trade name of BASF Wyandotte; tetra-functional block copolymers derived from the sequential addition of propylene oxide and ethylene oxide to ethylenediamine such as Tetronic 304 and Tetronic 908 Prill where Tetronic is a trade name of BASF Wyandotte; polymers comprised of N, N-dimethyl-1-hexadeanamine oxide dihydrate such as Admox 14-85, Admox SC-1685 and Admox 18-85 where Admox is a trade name of Ethyl Corporation; polyvinylpyrrolidone; alkylphenol ethoxylates such as octyl-, nonyl- or dinonyl- phenoxypolyethoxy ethanol, and polymers comprised of ethoxylated alcohols that range from 8 to 18 carbon atoms in length such as Neodol(R) 1-9 and Neodol (R) 25-9 where Neodol is a trade name of Shell Chemical Corporation.

The donor molecule of this invention is iodide anion. Suitable dry sources of iodide anion for this invention include sodium iodide and potassium iodide as well as other salts of iodide. Any source of iodide or iodide compound which yields iodide anion upon dissolution in an aqueous is suitable for this application. The simple salts of iodide are preferred and have the advantage of being less costly. Additionally, they both have a long shelf life in solid form. Iodide anion can be provided to the system in a liquid form if it is kept stable prior to use. Specifically, it is preferred not to contact the iodide anion with hydrogen peroxide. The concentration that will yield a suitable level of iodine varies with the pH of the contemplated formulation. However, the useful range is between 0.5 and 45.0 grams per liter in the final reconstituted formulation. The preferred range for iodide anions is between 0.20 and 1.9 grams per liter in the final reconstituted formulation. These ranges of iodide anion in conjunction with pH and the concentration of the other additives are anticipated to yield an equilibrium concentration of thiosulfate titrable iodine in the range of iodine is in the range of 10 to 12,500 ppm with a preferred range of 25 to 750 ppm.

The peroxidase enzyme of this invention is identified by the International Union of Biochemistry and the International Union of Pure and Applied Chemistry by the Enzyme Commission identification No. E.C. 1.11.1.7. Peroxidase can be obtained from a wide variety of sources. These sources include milk (lactoperoxidase) and human leukocytes (myerloperoxidase). The least expensive and most robust peroxidase suitable for this application is horseradish peroxidase. Commercially obtained peroxidase comes lyophilized as a dry powder which can then be admixed in a suitable carrier. It is anticipated that peroxidase that has been cloned from either horseradish, milk or human leukocytes will be suitable as a source of peroxidase for this application. Additionally, it has been observed that chemically modified peroxidase is suitable for use in this application. Modifications to the amino, carboxyl or carbohydrate moieties of peroxidase yield a suitable catalytic agent for inclusion in this application. The chemical modifications to peroxidase include cross-linking of enzyme molecules to each other, to solid surfaces or to other proteins. The chemical agents used for crosslinking include glutaraldehyde, maleimides, succinimides, carbodiimides, dicarboxylates, activated glycols, imidoesters, photoreactive azides and other agents known to one skilled in the art.

The aforementioned forms of peroxidase can be provided in a dry form such as the lyophilized peroxidase offered commercially or in a largely aqueous environment. If the peroxidase is supplied in an aqueous environment it typically will be incorporated into a medium that provides increased stability such as glycerol or other polyols or sugars with elevated viscosity. The peroxidase of this application can be combined with many additives whether it is supplied dry or in an aqueous environment. The concentration range that peroxidase can be used over is between 0.00005 and 0.5 mg/mL in the final composition. The preferred range is between 0.0005 and 0.01 mg/mL in the final composition.

The preferred oxidant of this invention is hydrogen peroxide. Any material which acts as a source of hydrogen peroxide when admixed in an aqueous environment is suitable for the present invention. The term "source of peroxide" for purposes of the present invention and as used hereafter shall mean any material alone or in combination which can serve as precursors for hydrogen peroxide including metal peroxides, percarbonates, persulphates, perphosphates, peroxyesters, urea peroxide, peroxyacids, alkylperoxides, acylperoxides and perborates. Alternatively methyl peroxide can also be used as a source of hydrogen peroxide. Mixtures of two or more of these substances can also be used. The concentration range for hydrogen peroxide in the final composition is between 0.0005 and 3% in the final composition. The preferred concentration for hydrogen peroxide is between 0.001 and 0.05% in the final composition.

The organic detergents and surfactants of this application include anionic, cationic, zwitterionic, non-ionic and ampholytic agents. These molecules are frequently used in formulations used for cleaning inanimate and animate surfaces. Representative compounds include sodium lauryl sulfate, lithium lauryl sulfate, alkyl benzenesulfonates, alkane sulfonates, alkene sulfonates, sulfated anionic detergents, sulfated anionic detergents, sulfonated anionic detergents, phosphated anionic detergents, carboxylated anionic detergents, Tween 20-polyoxyethylene sorbitan monolaurate, Tween 100, alkyl sulphates, alkyl ether sulphates, fatty acid amides, myristic acid, lauric acid, capric acid, caprylic acid, coconut and palm kernel fatty acids,, N-acyl-sarconsinates, sodium-N-acyl-N-methyl taurates, sodium cocoylisothioate and amidopropyl betaines.

Representative humectants and emollients suitable for inclusion in the compositions contemplated in this application include sorbitol, dulcitol, glycerol, propylene glycol, acetamidopropyl trimonium chloride, lactamidoprpyl trimonium chloride, acetamide MEA, lactamide MEA, lanolin, ethoxylated lanolins, polyethylene glycol-lanolin derivatives that contain lanolin dispersed onto polyethylene glycol, sorbitan isostearate, cetearyl octanoate, maleated soybean oil, cetyl lactate, lauryl lactate, dioctyl malate, myristyl lactate, tridecyl neopentanoate, glyceryl dilaurate, condensation products of primary and secondary alcohols, block polymers of ethylene oxide and propylene oxide and polyethylene glycol and polyethylene glycol derivatives.

Representative foam stabilizers and thickening agents suitable for inclusion in the compositions contemplated in this application include sodium dialkyl sulfosuccinates, carboxymethylcellulose, xanthan gums, methylcellulose, locust bean gum, carrageenan, and guar gum.

Suitable buffering agents for inclusion in the compositions contemplated in this application include water and hydroalcoholic mixtures buffered with glycine-glycine.HCl, potassium hydrogen phthalate-phthalic acid, citric acid-$Na_2HPO_4$, citric acid-$KH_2PO_4$-$H_3BO_3$-diethylbarbituric acid-NaOH, citric acid-sodium citrate, dimethylglutaric acid-sodium dimethylglutarate, acetic acid-sodium acetate, succinic acid-sodium succinate, potassium hydrogen phthalate-dipotassium phthalate, sodium cacodylate-cacodylic acid, sodium hydrogen maleate-disodium maleate, $Na_2HPO_4$-$NaH_2PO_4$, sodium bicarbonate-5% $CO_2$, imidazole-imidazole-HCl, boric acid-sodium borate and Tris.

It should be noted that it is not essential to the successful practice of this invention that the iodine level in a reconstituted formulation remain the same during the time that it is intended for use. Rather, what is important is that any change in iodine concentration be held within the limits of variation that will not effect a minimum performance level for the particular type product. The microbicidal iodine products considered to be within the scope of this present invention are those in which the pH will be less than 7.0 The preferred range for pH is between 4.5 and 6.5.

An important aspect of this invention is to add the iodine sequestrant at a point in time prior to equilibration of the enzymatic reaction. That is, the iodine sequestrant should be admixed in the germicide prior to the point in the reaction wherein the concentration of iodide anions does not substantially change. Specifically, the iodine sequestrant should be combined with the enzymatic reaction preferably when the concentration of iodide anions is within 20% of the equilibrium concentration.

The equilibrium concentration of iodine anions can be determined by monitoring the concentration of iodide anions as a function of time and fitting the data to an exponential curve of the type $I_t=I_0 \epsilon^{\lambda t}+K$: where $I_t$ represents the concentration of iodide anions at a time point represented by the subscript t; $I_0$ represents the concentration of iodide anions at the beginning of the reaction (i.e., the zero time point); $\epsilon$ is the base for Naperian logarithms; $\lambda$ is the time constant that describes the rate at which iodide anions are oxidized; K is a constant; and t is time. For the purposes of this application the equilibrium concentration of iodide anions is defined as the concentration of iodide anions at a time that is equal to 10 times the reactions time constant $\lambda$.

It is necessary to add the iodine sequestrant prior to establishment of the enzyme driven equilibrium in order to achieve substantial increases in the level of available iodine. If the iodine sequestrant is added after equilibrium is established there will not be a substantial increase in available iodine although it is possible that the stability of the formulation may be increased.

Various changes and modifications in the germicidal iodide anion, peroxide and peroxidase compositions herein disclosed may occur to those skilled in the art, and to the extent that such changes and modifications are embraced by the appended claims, it is to be understood that they constitute part of the present invention.

EXAMPLES

1. The following two stock solutions were prepared: stock solution A which contained 2.4 mg/mL sodium iodide, 0.01 mg/mL horseradish peroxidase and 19 mg/mL of sodium bicarbonate; and stock solution B which contained 20 mg/mL of anhydrous citric acid in 0.03% hydrogen peroxide. Pluronic F-127, Pluronic F87 Prill and Tetronic 908 Prill were added into separate vials that contained 50 mL of stock solution B so that the final concentration of each iodine sequestrant was 1% (w/v). Five mL of the stock B solutions that were made 1% (w/v) with respect to Pluronic F-127, Pluronic F87 Prill and Tetronic 908 Prill, were each added to a flask. A fourth flask was prepared that contained 5 mL of stock solution B without any iodine sequestrant; this flask served as a control. Five mL of stock solution B was added to each of the four flasks. The flasks were then incubated for 1 hour at room temperature and the level of thiosulfate titrable iodine was determined in each flask. The results of these measurements are shown below in Table I.

TABLE I

| Equilibrium Iodine (ppm $I_2$) Level versus Iodine Sequestrant | | | | |
|---|---|---|---|---|
| | Water/Control | F-127 | F87 Prill | 908 Prill |
| Enzymatic | 495 | 596 | 596 | 609 |
| pH | 5.42 | 5.4 | 5.42 | 5.5 |

The control sample did not contain an iodine sequestrant; the control contained 495 ppm of available iodine. In contrast, those samples with an iodine sequestrant had significantly elevated levels of thiosulfate titrable iodine. One skilled in the art known that iodine sequestrants do not elevate the level of thiosulfate titrable iodine in iodophors. Iodine sequestrants are used to mitigate some of the unpleasant effects that are observed at high iodine levels. Surprisingly, addition of an iodine sequestrant to applicant's chemistry prior to establishment of the final aqueous equilibrium resulted in an increase of approximately 100 ppm of thiosulfate titrable iodine. This increase cannot be explained by claiming a pH effects since all of the formulations had a final pH value that was within 0.1 pH unit. This increase of 100 ppm represents an addition of about 20% in usable iodine versus the control.

The reduction in the level of iodine atoms required to achieve a defined level of thiosulfate titrable iodine has potential commercial significance. This is due to the fact that iodine species, including iodide, represent a significant percentage of the overall raw material costs in most iodine-based germicides.

2. The effect of an iodine sequestrant on the level of available iodine was modeled theoretically in order to examine the effect that an iodine sequestrant would have on the equilibrium distribution of iodine species. Polyvinylpyrrolidone (PVP) was selected as the sequestrant for this analysis. PVP was selected because the mechanism of iodine binding to PVP has been studied and it is generally accepted that triiodide is form of iodine that is bound to PVP. The equilibrium constant between iodide, iodine and triiodide is known and therefore it is possible to calculate the solution phase concentration of these species.

The concentrations of iodide (i.e., Aq. I⁻), free elemental iodine (i.e., Aq. $I_2$), free triiodide (i.e., Aq. $I_3^-$) and PVP-bound triiodide (i.e., Bound-$I_3^-$) are shown below in Table II. The concentration of iodide, free elemental iodine and free triiodide in the absence of PVP was arbitrarily selected for purposes of illustration. The mass of iodine species is equivalent for all calculated experimental conditions. The concentration of PVP-bound triiodide was arbitrarily selected and varied from a concentration range that varied from 0 to 80% of the initial concentration of the free molecular iodine.

The molarity of available iodine was calculated as a function of increased triiodide binding to PVP. The results are shown below in Table II. The results indicate that the level of available iodine does not increase as the level of sequestered iodine is increased. This theoretical result is consistent with experimental observations. It is known that adding an iodine sequestrant to an aqueous solution of iodine does not increase the level of available iodine. In fact, one skilled in the art would anticipate that the available iodine level would decrease due to oxidation of said sequestrant.

TABLE II

Available Iodine Versus Sequestered Iodine

| Molarity of Bound-$I_3^-$ | 0 | 0.0001 | 0.0002 | 0.0003 | 0.0004 |
|---|---|---|---|---|---|
| Molarity of Aq.- I⁻ | 0.0005 | 0.00044 | 0.000377 | 0.000309 | 0.000237 |
| Molarity of Aq.- $I_2$ | 0.0005 | 0.00044 | 0.000377 | 0.000309 | 0.000237 |
| Molarity of Aq.- $I_3^-$ | 0.000177 | 0.000137 | 0.000101 | 0.000067 | 0.000039 |
| Molarity of Available Iodine | 0.000677 | 0.000677 | 0.000677 | 0.000677 | 0.000677 |

Experimental observations to confirm the theoretical analysis provided in Example 2 are shown below in Example 3.

3. The effect of Pluronic F127, Pluronic F87, Tetronic 908 and polyvinylpyrrolidone on the level of available was determined. Experiment 2 utilized a ratio of iodide to elemental iodine that was 1.0 to 1.0. This experiment uses ratios of iodide to elemental iodine that are both less than and greater than 1.0. This experiment was conducted to confirm that the addition of an iodine sequestrant to an aqueous iodine solution does not increase the level of available iodine.

TABLE III

Effect of Iodine Sequestrant on the Level of Available on Non-enzymatic Iodine Equilibria versus Iodine Sequestrants

| Ratio of Sodium Iodide to Elemental Iodine (NaI/$I_2$) | 1.37ᵃ | 1.0ᵇ | 0.95ᵇ | 0.91ᵇ |
|---|---|---|---|---|
| | | Available Iodine (ppm) | | |
| Control (no sequestrant) | 682 | 673 | 685 | 660 |
| 1% Pluronic F127 | 583 | 558 | 558 | 533 |
| 1% Pluronic F87 | 635 | 622 | 622 | 584 |
| 1% Tetronic 908 | 609 | 596 | 596 | 583 |
| 1% Polyvinylpyrrolidone | 615 | 622 | 622 | 596 |

ᵃ = sum of NaI + $I_2$ equaled 1.5 g/L.
ᵇ = sum of NaI + $I_2$ equaled 1.2 g/L.

A stock solution of 50 millimolar citric acid was buffered to pH 5.0 with sodium bicarbonate. Elemental iodine was dissolved in isopropanol at saturation and was used to provide elemental iodine to the reactions. A stock solution of sodium iodide in the citrate-carbonate buffer was prepared at a concentration of 0.75 g/L and used for preparation of the reaction solutions. The ratio of sodium iodide to elemental iodine was varied from 1.37 to 0.91. The mixtures were allowed to incubate at room temperature and the level of available iodine was determined at equilibrium. The results of this experiment are shown above in Table III.

The results indicate that addition of an iodine sequestrant to a solution of aqueous iodine does not increase the level of available iodine as compared to an identical solution of iodine that does not contain a sequestrant.

4. An experiment was designed to determine the effect of iodine sequestrants on the level of available iodine in peroxidase catalyzed reactions. Two stock solutions were prepared. Stock solution 1 contained 2.4 grams of sodium iodide, 0.01 grams of peroxidase (HRP) and 20 grams of sodium bicarbonate in 1 liter of water. Stock solution 2 contained 18.4 grams of anhydrous citric acid and 1 mL of 30% hydrogen peroxide.

One gram of Pluronic F127, Pluronic F87, Tetronic 908 and PVP were added to separate 100 mL volumetric flasks. Stock solution 2 was added to each of these volumetric flasks until the iodine sequestrants were in solution in a total volume of 50 mL. Fifty mL of stock solution 1 was mixed with the following: 50 mL of stock solution 2, 50 mL of stock solution 2 with Pluronic F127, 50 mL of stock solution 2 with Pluronic F87, 50 mL of stock solution 2 with Tetronic 908 and 50 mL of stock solution 2 with PVP. The level of available iodine in these reactions were determined after 90 minutes.

TABLE IV

Effect of Iodine Sequestrant Addition Before and After Equilibration of the Enzymatic Reaction

| Time of Sequestrant Addition | Sequestrant | pH | ppm $I_2$ |
|---|---|---|---|
| prior to HRP reaction | Pluronic F127 | 5.52 | 609 |
| prior to HRP reaction | Pluronic F87 | 5.54 | 609 |
| prior to HRP reaction | Tetronic 908 | 5.56 | 596 |
| prior to HRP reaction | Polyvinyl-pyrrolidone | 5.57 | 609 |
| after HRP reaction is equilibrated | Pluronic F127 | 5.68 | 406 |
| after HRP reaction is equilibrated | Pluronic F87 | 5.67 | 440 |
| after HRP reaction is equilibrated | Tetronic 908 | 5.65 | 440 |
| after HRP reaction is equilibrated | Polyvinyl-pyrrolidone | 5.67 | 440 |

Four additional peroxidase-based reactions were initiated using 50 mL of both stock solutions. After 1 hour 1 gram of each of Pluronic F127, Pluronic F87, Tetronic 908 and PVP were added to each reaction. The level of available iodine in these reactions were determined after 30 minutes. The results are shown below in Table IV and indicate that there is a substantial increase in available iodine when the iodine sequestrant is added prior to reaching equilibrium in the peroxidase reaction. It is not understood why addition of the iodine sequestrant prior to the establishment of an aqueous equilibrium results in an increase in the level of available iodine.

5. Various known iodine sequestrants were selected and their effect on the level of thiosulfate titrable iodine generated from the peroxidase, iodide, peroxide system of this application was examined. The iodine sequestrants were screened under identical conditions. All of these iodine sequestrants were added to the reaction prior to the establishment of the final aqueous iodine equilibria.

TABLE II

Effect of Iodine Sequestrants on Stability

| Additive | Grams per Lite | Initial Iodine (ppm) | % Iodine Remaining | | | | | | | | |
|---|---|---|---|---|---|---|---|---|---|---|---|
| | | | Day 5 | Day 7 | Day 10 | Day 12 | Day 17 | Day 20 | Day 25 | Day 28 | Day 31 |
| None (control) | | 605 | 95% | 95% | 94% | 91% | 82% | 75% | 71% | 64% | 60% |
| Polyox N-10 | 0.056 | 38 | 67% | 67% | 67% | 33% | 33% | 33% | 14% | — | — |
| Pluronic F-38 | 0.05 | 673 | 108% | 106 | 106% | 100 | 92% | 88% | 79% | 75% | 77% |
| Pluronic F108 | 11.8 | 964 | 99% | 99% | 99% | 99% | 99% | 99% | 96% | 93% | 91% |
| Tetronic 304 | 0.616 | 647 | 86% | 86% | 80% | 73% | 59% | 49% | 43% | 39% | — |
| Tetronic 304 | 0.308 | 622 | 94% | 94% | 88% | 82% | 71% | 63% | 59% | 55% | — |
| Tetronic 908 | 19.3 | 926 | 105% | 105 | 101% | 97% | 95% | 89% | 86% | 82% | 82% |
| Admox 14-85 | 0.6 | 584 | 89% | 80% | 70% | 54% | 24% | 20% | 15% | 11% | 0% |
| PVP | 20 | 825 | 95% | 86% | 82% | 77% | 68% | 58% | 54% | 52% | 52% |
| PVP | 4 | 863 | 100% | 99% | 96% | 94% | 91% | 85% | 82% | 81% | 79% |
| PVP | 2 | 723 | 88% | 81% | 79% | 77% | 74% | 70% | 68% | 68% | 67% |
| PVP | 0.4 | 609 | 100% | 100 | 98% | 96% | 90% | 83% | 81% | 75% | 75% |
| Neodol(R) 1-9 | 0.66 | 292 | 100% | 100 | 100% | 96% | 96% | 83% | 83% | 74% | — |

The pH of this screening experiment was 5.0. The experimental mixtures were established by mixing (a) ten mL of a selected iodine sequestrant at a known concentration, (b) 1.5 grams of sodium iodide, (c) 4.0 grams of anhydrous citric acid, (d) 0.5 milligrams of horseradish peroxidase and (e) 3.15 grams of sodium percarbonate in 990 mL of water. This mixture resulted in a pH of 5.0 and an initial hydrogen peroxide concentration of 0.080%. These chemicals were added to a glass jar with a rubber stopper. Samples were stored at room temperature. One mL samples of each mixture were withdrawn periodically over a month and measured to determine their level of thiosulfate titrable iodine. Results are shown in Table II below. The values indicated for the control represent the average of three different samples. The % iodine remaining was calculated by dividing the level of iodine on the indicated day by the level of iodine on day 1. A dashed line indicates that the experiment was not performed.

Polyox N-10 significantly reduced the level of iodine at concentrations above 0.0.05 g/L. Additionally, Polyox N-12K significantly reduced the level of iodine at concentrations above 1.5 g/L (data not shown). Pluronic F-38 increased the level of available iodine. Pluronic F108 Prill was also very effective at increasing both stability and iodine levels. Tetronic 304 at concentrations between 0 and 1.0 g/L provided a modest increase in available iodine levels. Tetronic 908 Prill was very effective at increasing both stability and iodine levels at concentrations above 15 g/L but stability and iodine levels were dramatically reduced at concentrations between 0.25 and 5.5 g. Admox 14-85 did not significantly effect the available. Polyvinylpyrrolidone (PVP) increased the stability of iodine at concentrations between 0.04 and 10 g/L. PVP did not diminish the iodine levels at any concentration tested. Neodol(R) 1-9 reduced the available iodine at concentrations between 0.5 and 2.5 g/L.

We claim:

1. A method of forming an iodine based germicide in situ in an aqueous based medium having a stabilized concentration of available iodine comprising the steps of combining a source of peroxide, a source of iodine ions, a peroxidase that falls within the class of peroxidase in the Enzyme Commission identification No. E.C. 1.11.1.7. and an iodine sequestrant selected from the group consisting of: polyvinylpyrrolidone, block copolymers of ethylene oxide and propylene oxide, alkylphenol ethoxylates, tetrafunctional block copolymers derived from the sequential addition of propylene oxide and ethylene oxide to ethylenediamine, copolymers of ethylene oxide and propylene oxide, and ethoxylated alcohols that range from 8 to 18 carbon atoms in length so as to form a non-reactive enzymatic composition, admixing said composition with an aqueous based medium to cause an enzymatic catalyzed reaction with said iodine sequestrant being added to said composition at a time prior to the equilibration of the enzymatic reaction such that the concentration of available iodine in said composition increases as compared to an identical composition without an iodine sequestrant.

2. A method as defined in claim 1 wherein the concentration of said peroxide is insufficient of itself to function as an agent in said composition for forming said iodine based germicide without the interaction of peroxidase.

3. A method as defined in claim 2 wherein the initial concentration of said peroxidase in said aqueous medium is in a range of between 0.00005 mg/mL and 0.5 mg/mL.

4. A method as defined in claim 2 wherein the initial concentration of said peroxide in said aqueous medium is in a range between 0.0005 and 3.0% by volume.

5. A method as defined in claim 1 wherein the concentration of said iodine anion upon admixture of said composition with said aqueous based medium is in a range of between 0.05 grams per liter and 45 grams per liter.

6. A method as defined in claim 5 wherein said non-reactive enzymatic composition further comprises buffer agent means to control the pH of said aqueous based medium in said solution with said composition at a pH of below 7.0.

7. A method as defined in claim 6 wherein the concentration of titratable iodine formed in said solution with said composition is at a pH of below 7.0.

8. A method as defined in claim 6 wherein said composition is at a pH between 4.5 and 6.5.

9. A method as defined in claim 8 wherein said buffer is selected from the group consisting of: glycine-glycine.HCl, potassium hydrogen phthalate-phthalic acid, citric acid-$Na_2HPO_4$, citric acid-$KH_2PO_4$-$H_3BO_3$-diethylbarbituric acid-NaOH, citric acid-sodium citrate, citric acid-sodium carbonate, dimethylglutaric acid-sodium dimethylglutarate, acetic acid-sodium acetate, succinic acid-sodium succinate, potassium hydrogen phthalate-dipotassium phthalate, sodium cacodylate-cacodylic acid, sodium hydrogen maleate-disodium maleate, $Na_2HPO_4$-$NaH_2PO_4$, sodium bicarbonate-5% $CO_2$, imidazole-imidazole.HCl, boric acid-sodium borate, Tris and mixtures thereof.

* * * * *